(12) United States Patent
Lary

(10) Patent No.: US 6,506,180 B1
(45) Date of Patent: Jan. 14, 2003

(54) PASSIVE PERFUSION SLEEVE/PLACEMENT CATHETER ASSEMBLY

(76) Inventor: Banning G. Lary, 6280 Sunset Dr., Suite 411, Miami, FL (US) 33143

(*) Notice: Subject to any disclaimer, the term of this patent is extended or adjusted under 35 U.S.C. 154(b) by 0 days.

(21) Appl. No.: 09/221,801

(22) Filed: Dec. 28, 1998

(51) Int. Cl.⁷ .................. A61M 31/00; A61M 37/00
(52) U.S. Cl. .................. 604/103.12; 604/101.04
(58) Field of Search ............ 604/96.01, 101.01, 604/101.02, 101.04, 103, 103.04, 103.05, 103.09, 164.01, 164.1, 915, 919, 921, 103.11–103.13; 606/192, 194, 108

(56) References Cited

U.S. PATENT DOCUMENTS

| | | | |
|---|---|---|---|
| 4,790,315 A | | 12/1988 | Mueller, Jr. et al. |
| 4,877,031 A | | 10/1989 | Conway et al. |
| 4,892,519 A | | 1/1990 | Songer et al. |
| 4,911,163 A | * | 3/1990 | Fina |
| 4,944,745 A | | 7/1990 | Sogard et al. |
| 4,976,710 A | * | 12/1990 | Mackin |
| 5,000,734 A | * | 3/1991 | Boussignac et al. |
| 5,032,113 A | | 7/1991 | Burns |
| 5,137,513 A | | 8/1992 | McInnes et al. |
| 5,158,540 A | | 10/1992 | Wijay et al. |
| 5,180,367 A | * | 1/1993 | Kontos et al. ......... 604/101.04 |
| 5,217,434 A | | 6/1993 | Arney |
| 5,221,260 A | | 6/1993 | Burns et al. |
| 5,232,446 A | | 8/1993 | Arney |
| 5,261,879 A | | 11/1993 | Brill |
| 5,295,995 A | | 3/1994 | Kleiman |
| 5,318,535 A | | 6/1994 | Miraki |
| 5,334,154 A | | 8/1994 | Samson et al. |
| 5,344,402 A | | 9/1994 | Crocker |
| 5,370,617 A | | 12/1994 | Sahota |
| 5,383,890 A | | 1/1995 | Miraki et al. |
| 5,403,274 A | | 4/1995 | Cannon |
| 5,433,706 A | | 7/1995 | Abiuso |
| 5,447,497 A | * | 9/1995 | Sogard et al. |
| 5,454,789 A | | 10/1995 | Burns et al. |
| 5,476,477 A | | 12/1995 | Burns |
| 5,484,408 A | | 1/1996 | Burns |
| 5,484,411 A | | 1/1996 | Inderbitzen et al. |
| 5,501,667 A | | 3/1996 | Verduin et al. |
| 5,505,702 A | | 4/1996 | Arney |
| 5,512,051 A | * | 4/1996 | Wang et al. |
| 5,522,800 A | | 6/1996 | Crocker |
| 5,531,689 A | | 7/1996 | Burns et al. |
| 5,536,250 A | | 7/1996 | Klein et al. |
| 5,542,926 A | | 8/1996 | Crocker |
| 5,562,620 A | | 10/1996 | Klein et al. |
| 5,571,089 A | | 11/1996 | Crocker |
| 5,573,508 A | | 11/1996 | Thornton |
| 5,573,509 A | | 11/1996 | Thornton |
| 6,132,397 A | * | 10/2000 | Davis et al. |
| 6,254,570 B1 | * | 7/2001 | Rutner et al. |

* cited by examiner

*Primary Examiner*—Anhtuan T. Nguyen
*Assistant Examiner*—LoAn H. Thanh
(74) *Attorney, Agent, or Firm*—Michael E. Klicpera

(57) ABSTRACT

A passive perfusion sleeve/placement catheter assembly for performing coronary angioplasty allows prolonged dilatations without blocking blood flow. The perfusion sleeve comprise an elongated shaft with a distally mounted composite balloon including a semi-rigid inner material surrounded by a more flexible and expandable outer material which can extend radially from the catheter and engage the vessel wall and atheroma. The semi-rigid inner material requires more pressure to cause distention than the outer expandable material thereby defining a blood flow channel. The perfusion sleeve/placement catheter assembly of the present invention includes a perfusion sleeve apparatus having a multiple lumen shaft and an expanding balloon connected to a distal end of the shaft. A placement catheter is employed to assist in delivery and retraction of the sleeve. The passive perfusion sleeve provides for optimum blood flow through the blood flow channel when the balloon is inflated and the placement catheter is proximally retracted.

20 Claims, 5 Drawing Sheets

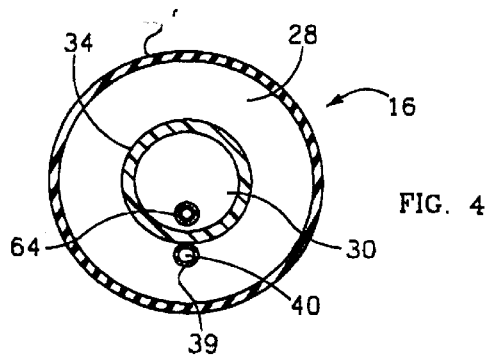
FIG. 4
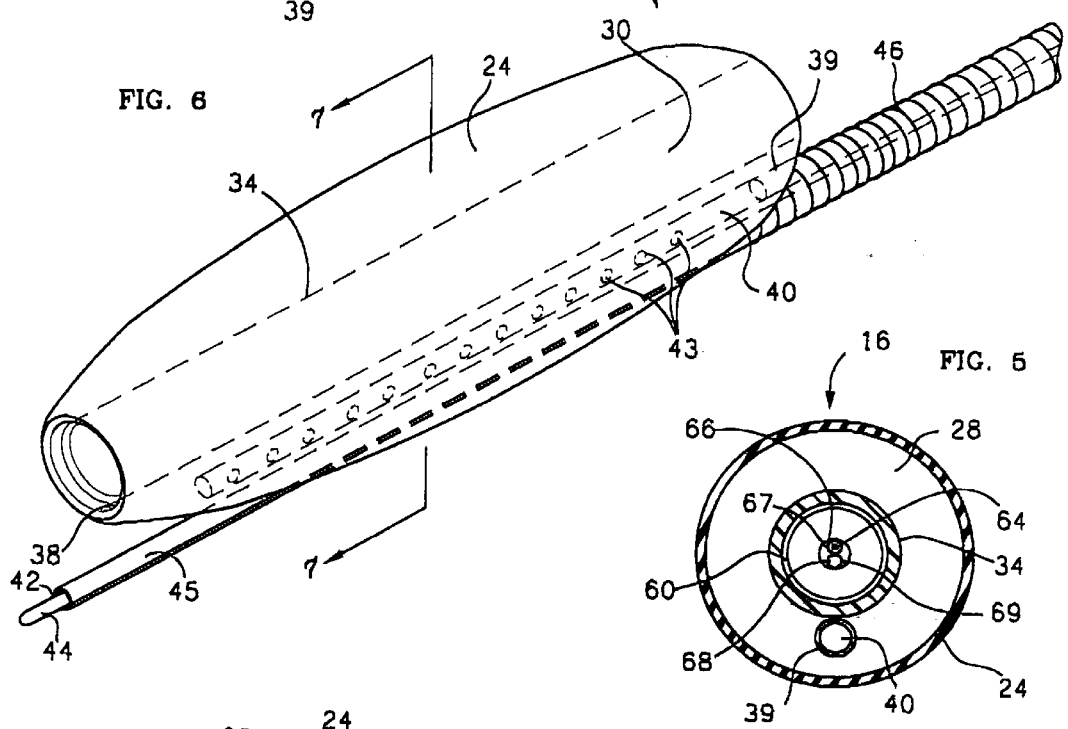
FIG. 6
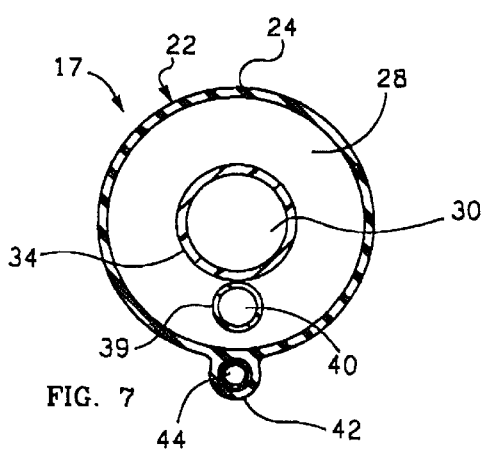
FIG. 7
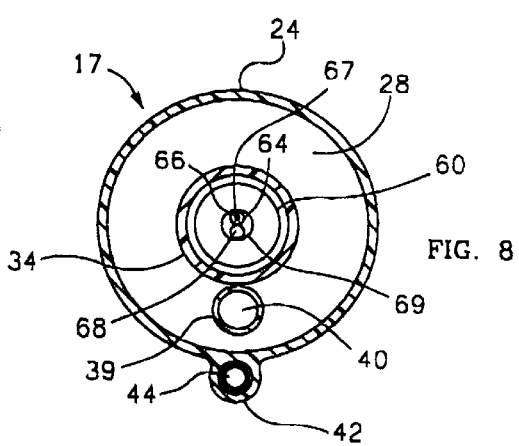
FIG. 5
FIG. 8

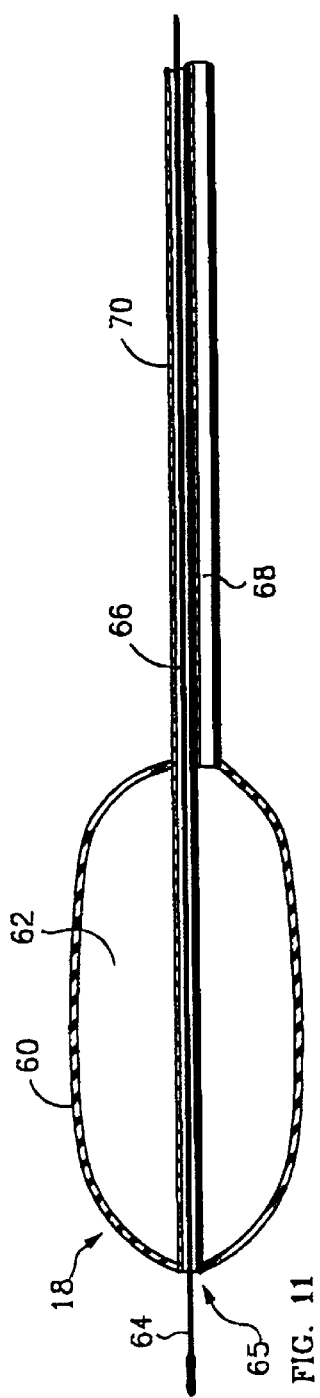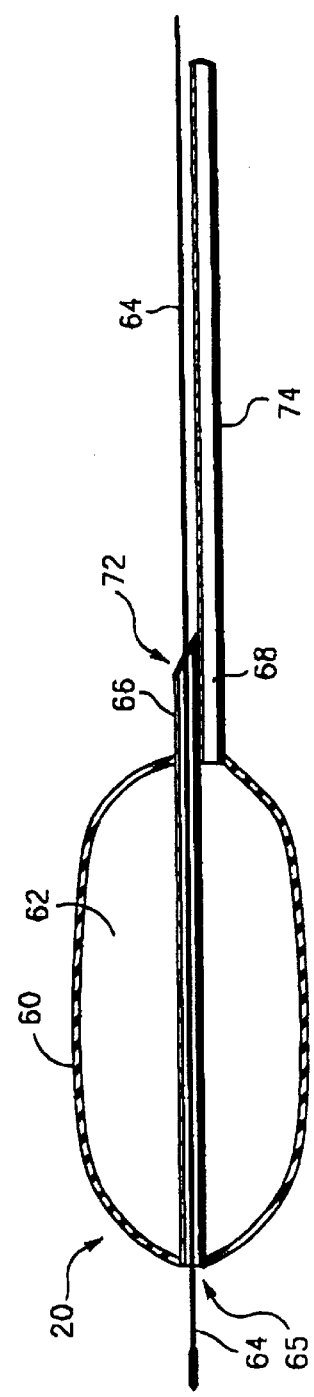

PASSIVE PERFUSION SLEEVE/PLACEMENT CATHETER ASSEMBLY

FIELD OF THE INVENTION

In general, the present invention relates to percutaneous transluminal devices and methods which are used treat obstructed (sclerotic) vessel lumina in humans. Furthermore, the present invention permits a continuous flow of blood during the procedure. In particular, the present invention relates to a perfusing sleevetballoon catheter apparatus which provides prolonged dilatations without blocking blood flow by use of passive perfusion.

BACKGROUND OF THE INVENTION

Cardiovascular disease is commonly accepted as being one of the most serious health risks facing our society today. A blood vessel of the human circulatory system can often become narrowed whereby the flow of blood is severely limited. The location of the narrowed blood vessel is commonly referred to as the stenotic region and is generally caused by growth or hyperplasia of the surrounding vessel wall tissues sometimes referred to as atheroma. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, alternative methods are available for treating cardiovascular disease percutaneously. Balloon angioplasty is accepted as an efficient and effective method for treating types of vascular diseases. In particular, balloon angioplasty is widely used for dilating stenotic regions in coronary arteries, although it is also used for treatment of stenoses in other parts of the vascular system including the peripheral vessels of the legs and kidneys and the carotid arteries in the neck. The most widely used form of balloon angioplasty is percutaneous transluminal coronary angioplasty (PTCA) and makes use of a guidewire, guide catheter and dilatation catheter which has an inflatable balloon at its distal end. Using fluoroscopic control, the physician first positions a guidewire to and beyond the stenotic region of interest. The physician then threads the catheter over the guidewire, advancing it through the vascular system until the distal balloon is positioned across the stenosis. The balloon is then inflated by supplying fluid under pressure through an inflation lumen in the catheter body. The expansion of the balloon dilates the vessel typically reestablishing acceptable blood flow through the vessel. Often balloon angioplasty is followed by the implantation of a stent to maximize and maintain the vessel patency after primary dilatation.

An initial concern about PTCA was the temporary blockage of blood flow during balloon inflation caused ischemic conditions distal to the balloon. As cardiologists gained clinical experience with PTCA, it became common knowledge that the vast majority of patients tolerate 30 to 60 second dilatations quite well. Concurrently, cardiologists discovered that prolonged dilatations can help overcome certain kinds of complications encountered with the angioplasty. Prolonged dilatations of several minutes are used to deal with dissections, perforations, intimal flaps, acute thrombosis and vessel spasms. The profound ischemia of a long dilatation is outweighed by the potential prevention of emergency coronary bypass surgery or the expense of deploying a permanent stent.

In the prior art, methods for enabling prolonged dilatations have been cumbersome, have been experimental, or have had potentially harmful side effects. Consequently, there has been no definitive study of the effects of prolonged dilations on the efficacy of PTCA.

In order to perform prolonged dilatations, several approaches have been suggested. These include the use of pharmacologic agents to improve myocardial tolerance of ischemia, synchronized retroprofusion, mechanical pump distal perfusion, and auto or passive perfusion.

The use of pharmacologic agents treats the symptoms of ischemia, but not the cause. As a result, this approach is inherently limited.

Synchronized retroprofusion involves pumping blood during diastole into the coronary sinus and then subselectively into the regional coronary veins which drain the jeopardized myocardium. This approach potentially offers nearly complete myocardial perfusion. The disadvantage of synchronized retroprofusion, however, is that it is complicated and cumbersome.

Mechanical pump distal perfusion involves pumping blood (or other perfusate) through a lumen of the PTCA catheter. The need to pump through the PTCA catheter requires some form of mechanical pump, and complicates the angioplasty equipment and procedure.

With passive perfusion, the balloon catheter acts as a temporary stent. Passive or auto perfusion catheters which have been proposed in the past have used a design similar to "bail out" catheters. On group of passive perfusion devices incorporate side holes in the catheter through a defined lumen proximal and distal to the balloon. These catheters, however, have several limitations. First, blood flow through the balloon may be suboptimal for many clinical situations (such as distal lesions and hypotension). And second, this configuration usually requires that the guidewire be retracted from the catheter lumen to maximize the flow of blood.

SUMMARY OF THE INVENTION

The perfusion sleeve/placement catheter assembly of the present invention includes 1) a perfusion sleeve apparatus having a multiple lumen shaft and an perfusion sleeve connected to a distal end of the shaft and 2) a placement catheter having a multiple lumen shaft and an expanding balloon connected to a distal end of the shaft.

The perfusion sleeve comprise a composite balloon including a semi-rigid inner material surrounded by a more flexible and expandable outer material which can extends radially from the catheter and engage the vessel wall and/or atheroma. The semi-rigid inner material requires more pressure to cause distention than the outer expandable material. When fluid is injected to fill the cavity defined by the joined outer and inner materials, distention of the outer balloon material exerts pressure to the wall of the vessel resulting in an angioplasty dilation while the inner balloon material resists distention and maintains a blood flow lumen. The perfusion sleeve can include a means attached and located on the outer balloon material to cooperated with a separate guidewire.

The placement catheter apparatus comprises a multiple lumen shaft with a standard expandable balloon connected to the distal end. The placement balloon is inflated to engage the inner material of the composite sleeve balloon to 1) facilitate placement of the assembly into vessel segment 2) to provide support to the inner material of the composite balloon to minimize distension into the blood flow lumen during inflation of the sleeve's composite balloon, and 3) to assist in the removal of the perfusion sleeve from a vessel segment. When the balloon of the placement catheter is deflated, it can be removed from the perfusion sleeve and retracted along the guidewire. When the placement catheter is retracted, the perfusion sleeve defines a longitudinal channel through which blood can flow. The balloon on the perfusion sleeve can be inflated prior to retraction of the placement catheter to restrict migration of the perfusion sleeve within an arterial or venous segment. The blood flow channel is generally aligned with a longitudinal length of the sleeve apparatus and in the preferred embodiment, the guide wire from the placement catheter extends through the sleeve lumen and out the distal end. The placement catheter also can comprise a rapid exchange design.

In operation, the balloon on the perfusion sleeve is deflated with the placement catheter balloon partially inflated to engage the inner surface of the perfusion sleeve but not fully to minimize the overall profile. The over-the-wire embodiment is advanced over a previously placed guidewire until the assembly is located within the desirable vessel segment. The placement catheter is then fully inflated. The expandable outer portion of the perfusion sleeve is inflated to maximize the engagement with the vessel wall performing a angioplasty dilation. The placement catheter is then deflated and retracted from the lumen of the perfusion sleeve. Blood is allowed to perfuse through the blood flow lumen of the perfusion sleeve for long durations.

When removal of the perfusion sleeve is desired, the placement catheter is advanced, with the distal balloon deflated, until it becomes centered within the perfusion sleeve. Radiopaque markers are provided on both the perfusion sleeve and in the balloon of the placement catheter to assist in identifying proper alignment and insertion of the assembly. When proper alignment is achieved, the balloon of the perfusion catheter is re-inflated and the expandable portion of the perfusion sleeve is deflated and the placement catheter/perfusion sleeve assembly is retracted and removed from the blood vessel as a unit.

It is an object of the present invention to be used as a routine angioplasty catheter to decrease a stenosis within a blood vessel but at the same time permitting much longer dilation time without the occurrence of ischemia events.

It is another object of the present invention to provide a gradual increase in dilation pressures without a significant decrease of blood flow thereby decreasing vessel wall injury or complications such as dissection, perforation or vessel trauma.

It is another object of the present invention to provide a longer dilation time to decrease the incidence of "rebound" phenomena.

It is another object of the present invention to provide a longer dilation time to alleviate complications such as dissections and flap formations allowing normal tissue glue and normal processes to repair the vessel.

It is another object of the present invention to decrease the general the use of anticoagulants associated with the angioplasty procedure.

BRIEF DESCRIPTION OF THE DRAWINGS

FIG. 4 is a cross-sectional view along Section 4—4 of FIG. 3.

FIG. 5 is a cross-sectional view along Section 4—4 of FIG. 3 with the placement catheter and placement catheter guidewire located within the flow passage.

FIG. 6 is a sectional view of the distal portion of another embodiment of the perfusion sleeve of FIG. 1 having a guidewire support external to the flow passage.

FIG. 7 is a cross-sectional view along Section 7—7 of FIG. 6.

FIG. 8 is a cross-sectional view along Section 7—7 of FIG. 6 with the placement catheter and placement catheter guidewire located within the flow passage.

FIG. 11 is a sectional view of the placement catheter with distally mounted expandable balloon with internal guidewire support.

FIG. 12 is another embodiment of the placement catheter with distally mounted expandable balloon having a rapid guidewire exchange capability.

DESCRIPTION OF THE PREFERRED EMBODIMENT

Figure 1:
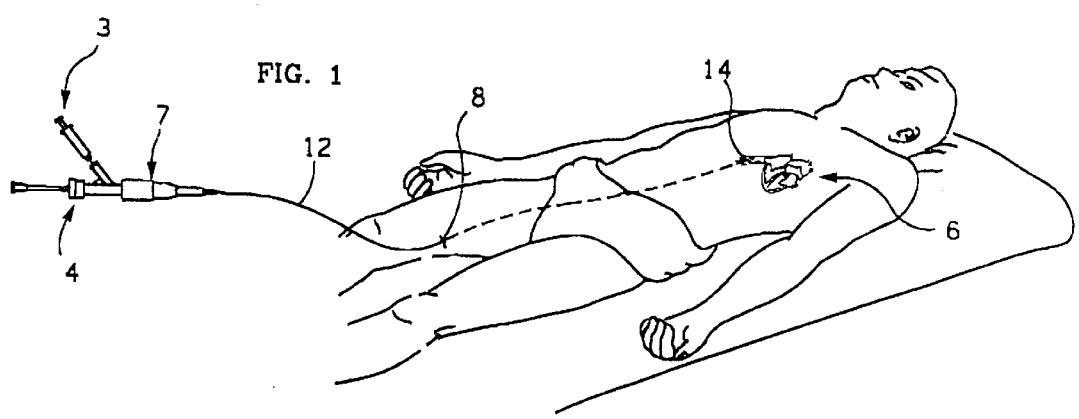
FIG. 1 shows the passive perfusion sleeve/placement catheter assembly of the present invention in a coronary setting.

Passive perfusion sleeve/placement catheter assembly shown in FIG. 1 shows the preferred embodiment of the passive perfusion sleeve/placement catheter assembly 14 in a coronary application 6 with percutaneous entry 8. It is also contemplated by the Applicant that the device can be indicated for use in peripheral vessels such as those in the legs or kidneys or neurological vessels.

The preferred embodiment of passive perfusion sleeve/placement catheter assembly 16 represented in FIGS. 2–5, 9 and 13–14 includes two independent yet interacting apparatuses. The perfusion sleeve as shown in FIGS. 2–5 has three major elements; a proximal manifold 7, an elongated multi-luminal shaft 12, and a composite balloon structure 16. Placement catheter 18 and 20 shown in FIGS. 11 and 12 respectively, also has three major elements; a proximal manifold 9, an elongated multi-luminal shaft 46, and a distal expandable balloon 60.

Figure 2:
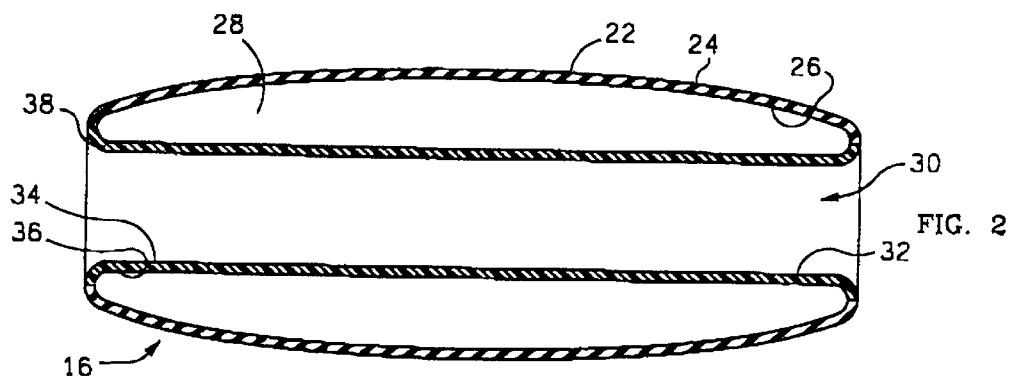
FIG. 2 is a cross-sectional view of a distal portion of the composite construction of the perfusion sleeve detailing the semi-rigid inner material surrounded by a flexible and expandable outer material.

As detailed in FIG. 2, the perfusion sleeve comprises a composite balloon 16, wherein an inner semi-rigid structure 34 having an first surface 32 adjacent to a perfusion lumen 30 and a second surface 36 adjacent the sleeve inflation lumen 28, is affixed to a flexible balloon outer material 24 having an inner facing surface 26 and an outer facing surface 22 which surrounds inner semi-rigid structure 34 forming a composite balloon structure or sleeve 16. The perfusion lumen or blood flow passage 30 of the inner semi-rigid structure 34 defines a main blood flow channel which extends longitudinally through perfusion sleeve 16. An inflation lumen 28 is formed between the inner semi-rigid structure 34 and the outer flexible material which comprises an expandable balloon 24. Inflation lumen 28 is in fluid communication with the inflation lumen 40 which terminates as a single open port 41 at the terminal end of the sleeve's inflation tube 39 as shown in FIGS. 3, 9 and 13–14. The inflation port also can comprise one or more inflation ports 43 as shown in more detail in FIGS. 6 and 10.

Inner semi-rigid structure 34 can be fabricated from a number of polymers forming a substrate or platform for the outer expandable balloon material or can consist of a relatively flexible polymeric material surrounded, encapsulated or otherwise supported by a semi-rigid material, such as metallic weave, braid or flat ribbon. The material for the inner structure 34 should be considerably less flexible and expandable than the outer material 24 such that when pressure is increased within sleeve inflation lumen 28, expansion occurs primarily from flexing the outer material 24 radially outward. The relatively less flexible inner structure 34 will remain relatively rigid resisting any tendency to expand radially inward into the blood flow lumen 30. In addition, the inner semi-rigid structure 34 and the outer expandable balloon 24 should be from compatible materials that are capable of being affixed together by standard technology, such as applying an adhesive to the mating surfaces of each material or welding the two structures together. The inner semi-rigid structure 34 consists of common reinforced or non-reinforced polymeric materials such as high density polyethylene, nylon, and PET. The flexible and expandable polymeric outer material 24 consists any of the common materials used in expandable balloons, such as polyethylene, polypropylene, nylon, or PET. The inner semi-rigid and outer flexible and expandable balloon portions can be fabricated from the same material where the wall thickness is increased for the semi-rigid portion or a reinforcing means, such as braid or coil engagement, can be applied to the inner semi-rigid material to provide the capacity to resist distending. Furthermore, the inner semi-rigid structure 34 can be fitted with one or more radiopaque markers (not shown) to assist in visualizing the position of the assembly within a vessel segment when utilized in a clinical procedure.

A means 38 to permanently affix the outer expandable and flexible balloon material 24 to the inner semi-rigid structure 34 is employed to withstand stresses associated with increasing the internal pressure of sleeve inflation lumen 28. It is necessary that the affixing process create a fluid tight seal between the two materials and restricting any delamination along the seal line during prolong periods of working pressures. The two materials can be joined by an adhesive process, such as a cyanoacrylate, epoxy or urethane compounds, or joined by a heat treatment process that melts and welds the two materials together.

Figure 3:
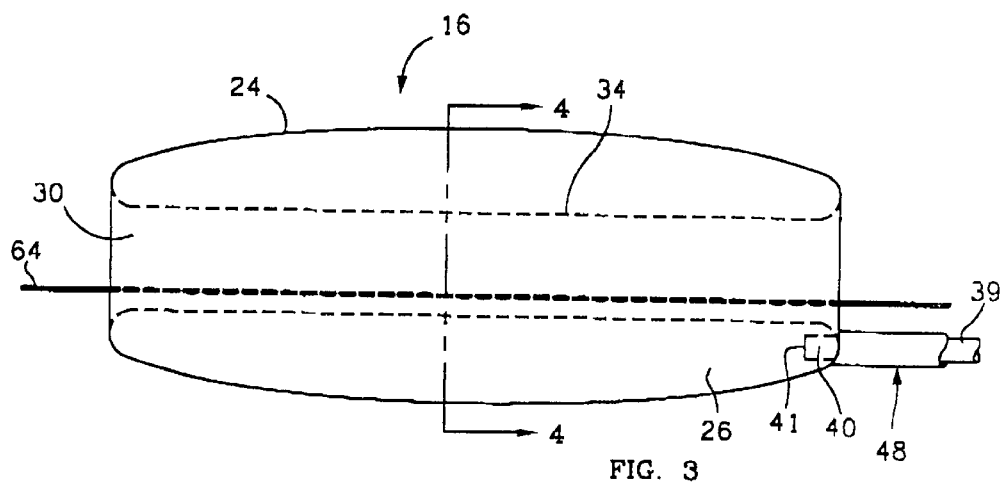
FIG. 3 is sectional view of a distal portion of preferred embodiment of the passive perfusion sleeve of FIG. 1 with a guide wire positioned within the blood flow lumen.

As shown in FIG. 3, the perfusion sleeve in engaged to shaft 48 which is a tubular structure having at a least a one lumen comprising catheter 12 of FIG. 1. The proximal portion of sleeve 16 is shaped to receive a distal portion of inflation lumen 40. As best shown in FIGS. 3–5 and 9, the inflation lumen 40 terminates near the proximal end of the perfusion sleeve in a single open port 41. In this primary embodiment of perfusion sleeve catheter 16, shaft 48 can be a single lumen tubular structure containing inflation lumen 40. In another design shown best in FIGS. 6–8 and 10, an inflation tube 39 containing inflation lumen 40 extends parallel to the blood flow channel 30 and terminates in plurality of inflation ports 43. A independent guide wire tube 45, having a guidewire lumen 42, runs parallel to inflation tube 39 and extends slightly beyond the distal end of perfusion sleeve 17 . In this alternate embodiment of perfusion sleeve catheter 16, shaft 48 can be a multi-lumen tubular structure containing inflation tube 39 with inflation lumen 40 and guidewire tube 45 including a lumen 42. In either case, the proximal portion of shaft 46 is bonded together with the perfusion sleeve to prevent separation. This type of bond is commonly known in the prior art and is formed by suitable adhesive, such as an epoxy or urethane.

Shafts 46 and 48 can be fabricated from polymers such as polyethylene, PET, nylon and can be reinforced by methods that are commonly known by the ones skilled in the art to increase its strength. Shafts 46 and 48 can be braided, surrounded with a coil or contain a metallic or polymer support line to increase the pull strength of the shaft. While the present invention is contemplated to be inserted into and retracted from a blood vessel with the perfusion sleeve and placement catheter engaged together as a unit, shafts 46 and 48 of the perfusion sleeve must possess sufficient strength to allow retraction of the sleeve from the blood vessel without assistance from the placement catheter for obvious reasons. Furthermore, the alternate embodiment of the perfusion catheter includes a guidewire lumen 42 which extends along the longitudinal axis of the multi-lumen shaft 46 of perfusion sleeve 16.

At its distal end, inflation lumen 40 is in fluid communication with the interior inflation lumen 28 of sleeves 16 or 17. Radiopaque or other fluid is supplied under pressure from an inflation device (not shown) which is connected to inflation port 3 of manifold 7. A single inflation port 41 or more inflation ports 43 are in fluid communication with inflation lumen 40, creating a fluid communication between inflation lumen 40 and sleeve inflation lumen 28. Fluid under pressure can enter from the inflation lumen 40 to the sleeve inflation lumen 28, causing the lumen and outer flexible and expandable material 24 to expand. When a vacuum is applied to the inflation lumen 40, fluid is withdrawn from the sleeve inflation lumen 28 causing the lumen and outer flexible and expandable material 24 to retract.

FIGS. 3, 4 and 5 demonstrate the preferred embodiment of a perfusion sleeve 16. In the embodiments disclosed in FIGS. 3–5, the guidewire extends from a terminal port 65 in the guidewire lumen 66 of the placement catheter 18 or 20. No guidewire support means is provided within the perfusion lumen 30. Therefore the guidewire is not fixedly engaged to the sleeve at any point but allowed to aligned itself with terminal port 65 of the placement catheter as described in more detail below. After exiting port 65, the guidewire enters the proximal end of the blood flow channel 30 is allowed to position itself freely within channel 30 and exiting the distal end.

FIG. 4 is a cross-sectional view taken from FIG. 3 detailing the physical location and cooperation of the perfusion lumen 30, semi-rigid inner member 34, sleeve inflation lumen 28, outer flexible and expandable material 24. At the very proximal end, inflation lumen 40 is secured to the sleeve. Also shown is the placement catheter guidewire 64 located within the perfusion lumen 30.

FIG. 5 is a cross-sectional view taken from FIG. 3 with the placement catheter inflated within the blood flow passage 30 of FIGS. 2–4. FIG. 5 details the physical location and cooperation of the placement catheter inflation lumen 68 with placement catheter guidewire 64 centrally located within placement catheter balloon 60. Also shown is the relationships between the placement catheter flexible balloon 60 and semi-rigid inner material 34, sleeve inflation lumen 28, outer flexible/expandable balloon material 24, and inflation lumen 40 with each other.

In the alternate embodiment as shown in FIGS. 6, 7 and 8, positioned external to the flexible and expandable portion 24 of the perfusion sleeve 17, is a guidewire lumen 42 designed to contain and facilitate tracking of a previously positioned perfusion sleeve guidewire 44. The individual guidewire tubular structure 45 includes a lumen 42 that is encased within multi-lumen catheter shaft 46 and extends along the longitudinal axis of the shaft 46 and perfusion sleeve 16 from the proximally positioned manifold 7 to the terminal exit of the perfusion sleeve. The primary difference between the preferred embodiment disclosed in FIGS. 3–5 and this alternate embodiment is the addition of this guidewire lumen positioned on the outside of the perfusion sleeve. The composite sleeve having an inner semi-rigid tubular material and external flexible and expandable material is identical as previously disclosed. Furthermore, the inflation lumen 40 and inflation port(s) 43, and the fluid communication with the sleeve inflation lumen 28 and catheter shaft 47 is the same as previously discussed for the embodiment in FIGS. 3–5.

FIG. 7 is a cross-sectional view taken from FIG. 6 detailing the physical location and cooperation of the perfusion lumen 30, semi-rigid inner member 34, sleeve inflation lumen 28, outer flexible and expandable material 24. As depicted in FIG. 6, shaft 46 is secured to the proximal end of perfusion sleeve 17. In addition, the physical relationship of inflation tubular structure 39 with inflation lumen 40 to semi-rigid structure 34 of sleeve 17. Also shown is the perfusion sleeve guidewire tubular structure 45 and guidewire 44 engaged to the outer surface 22 of flexible portion 24.

FIG. 8 is a cross-sectional view taken from FIG. 6 with the placement catheter inflated within the flow passage 30 of perfusion sleeve 17. FIG. 8 details the physical location and cooperation of the placement catheter's inflation tubular structure 69 including lumen 68 and placement catheter's guidewire tubular structure 68 having a lumen 66 and containing placement catheter guidewire 64, all three structures centrally located within placement catheter-balloon 60. Also shown is the relationships of the semi-rigid inner material 34, sleeve inflation lumen 28, outer flexible and expandable balloon material 24, and inflation lumen 40 with each other. In addition, FIG. 8 also shows the location of the perfusion sleeve guidewire lumen 42 containing guidewire 44.

Located at the proximal end of the catheter shaft 46 is a manifold 7 which includes an inflation port 3 and guidewire port 4 connected to catheter shaft 46. A stopcock valve (not shown) may be mounted on inflation port 3. As shown in FIG. 1, shaft 46 extends from the manifold to the perfusion sleeve and a fluid communication is established through inflation port 3, multi-lumen shaft 12 and to composite balloon/sleeve 16.

Figure 9:
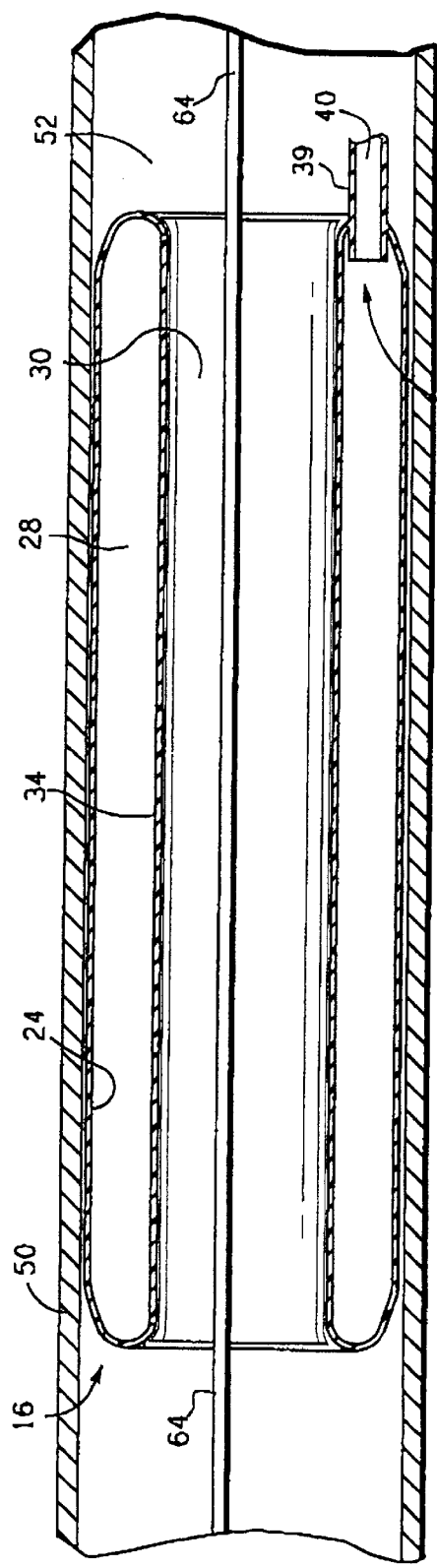
FIG. 9 is a sectional (sagittal) view of a distal portion of the passive perfusion sleeve of FIG. 3 positioned within a vessel segment with the placement catheter guidewire positioned within the flow passage.
Figure 13:
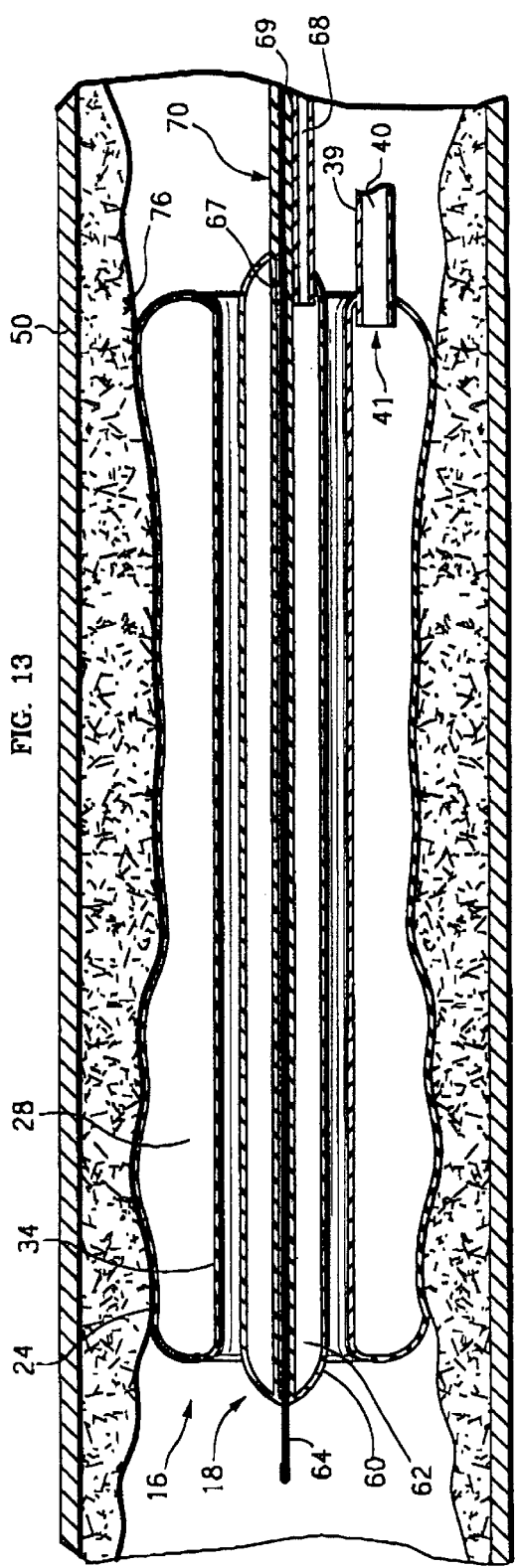
FIG. 13 is a sectional (sagittal) view of the passive perfusion sleeve/placement catheter assembly with the placement catheter positioned within the sleeve and the assembly located within a diseased segment of a vessel.
Figure 14:
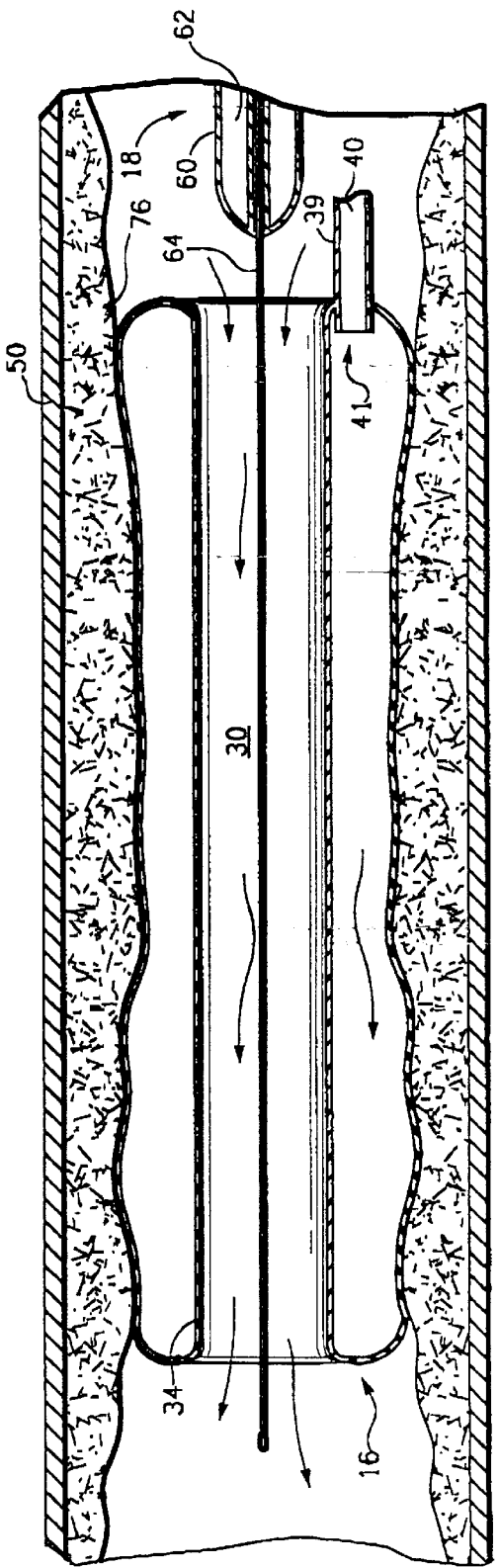
FIG. 14 is a sectional (sagittal) view of the passive perfusion sleeve/placement catheter assembly with the placement catheter retracted proximally along the guidewire allowing perfusion of blood through the perfusion sleeve inner lumen.

FIG. 9 shows the preferred embodiment of the perfusion sleeve in a blood vessel segment with the placement catheter of the present invention retracted and not shown. Infusing fluid through the inflation lumen 40 and out of the inflation port 41 fills the sleeve inflation lumen 28, causing the sleeve 16, and more specifically, the outer flexible material 24, to expand. In this configuration, the expandable and flexible material 24 of the sleeve engages and is in physical contact with the vessel wall 50 and/or stenosis 76 (as shown in FIGS. 13–14), thereby either dilating the stenosis within the vessel segment or restricting the sleeve from migrating from the present position. In the expanded configuration, blood flow from the vessel lumen 52 can enter the proximal end of sleeve flow channel 30, and exit the distal end. Placement catheter guidewire 64 is shown entering the perfusion lumen 30 from the proximal end and exiting the distal end.

Figure 10:
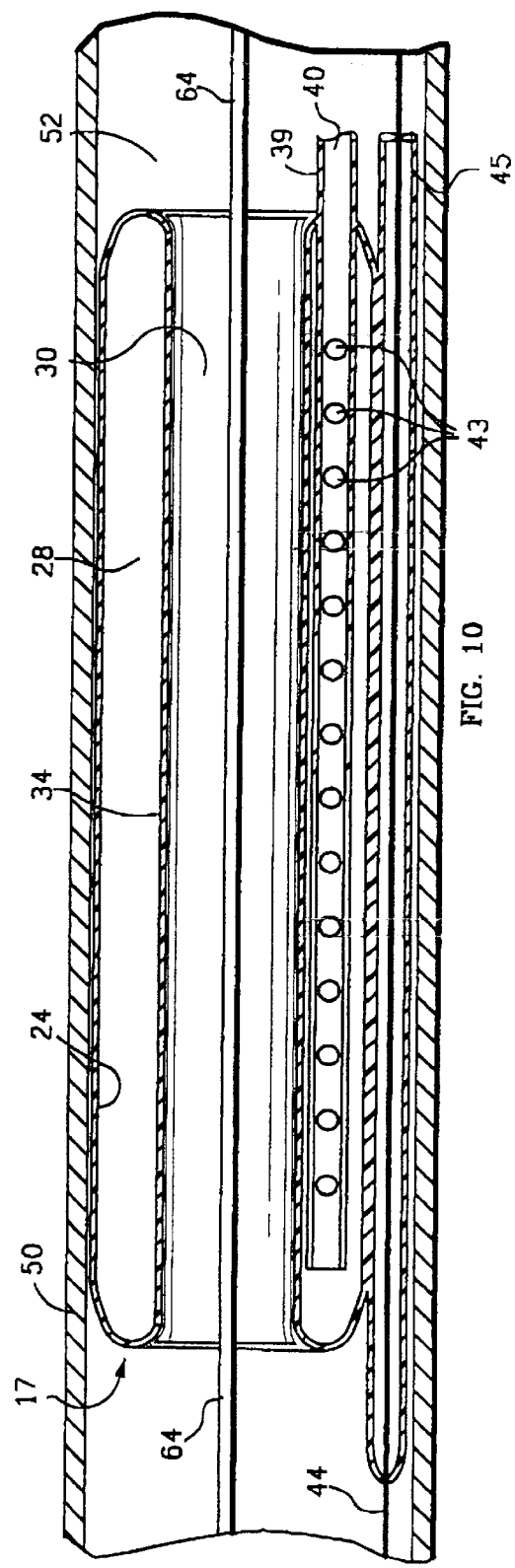
FIG. 10 is a sectional (sagittal) view of a distal portion of another embodiment of the passive perfusion sleeve of FIG. 6 having external guidewire support and positioned within a vessel segment with the placement catheter guidewire positioned within the flow passage.

FIG. 10 shows the alternate embodiment of the perfusion sleeve in a blood vessel segment with the placement catheter of the present invention retracted and not shown. Infusing fluid through the inflation lumen 40 and out of the inflation ports 43 fills the sleeve inflation lumen 28, causing the alternate sleeve 17, and more specifically, the outer flexible material 24, to expand. In this configuration, that the expandable and flexible material 24 of the sleeve engages and is in physical contact with the vessel wall 50 and/or stenosis 76 (as shown in FIGS. 13–14), thereby either dilating the stenosis within the vessel segment or restricting the sleeve from migrating from the present position. In the expanded configuration, blood flow from the vessel lumen 52 can enter the proximal end of sleeve flow channel 30, and exit the distal end. Placement catheter guidewire 64 is shown entering the perfusion lumen 30 from the proximal end and exiting the distal end. Also shown in FIG. 10 is the perfusion sleeve guidewire lumen 42 secured to the sleeve 17 containing perfusion guidewire 44.

FIGS. 11 and 12 show two embodiments of the placement catheter of the present invention. In general, the placement catheter comprises a multi-luminal elongate shaft 70 having a placement catheter inflation lumen 68 and a placement catheter guidewire lumen 66, a distally located expandable balloon 60 with balloon lumen 62. A placement catheter manifold is in fluid communication with inflation lumen 68 and in close proximity to the guidewire lumen 66 throughout the length of the placement catheter shaft 70. Also shown is guidewire 64 entering straight through the manifold to allow for easy transition into the lumen which extends along the length of the catheter shaft 70 and eventually terminating the distal end of the balloon from termination port 65. In FIG. 11, an over-the-wire design of the placement catheter 18 is depicted. In the over-the-wire design, the guidewire is contained with the guidewire lumen 66 which extends over the entire length of the catheter shaft 70. The catheter shaft can be comprised from standard polymeric materials such as polyethylene or nylon and can have be reinforced by standard means known by those skilled in the art. The balloon can be fabricated from polyethylene, PET, PEN, or nylon. In FIG. 12, an alternate embodiment of the placement catheter 20 is disclosed which employs a design having rapid exchange capability. This rapid exchange placement catheter 20 is identical to the embodiment in FIG. 9 with the exception of a shorten guidewire lumen which terminate near the proximal end of the balloon. An guidewire entry port 72 can be specifically configured to facilitate the insertion of the guidewire. Also, the rapid exchange catheter shaft design 74 does not have to be multi-luminal thereby reducing its overall profile. The rapid exchange placement catheter 20 can be fabricated from the same materials used to manufacture the over-the-wire design 18.

FIG. 13 shows the preferred design of the present invention positioned within a diseased arterial segment 50. In this diagram, the perfusion sleeve 16 is inflated with a fluid that entered from catheter inflation lumen 40 into the sleeve inflation lumen 28, causing the semi-rigid member 24 to expand and contact the atherosclerotic plaque 76 in vessel 50. The semi-rigid member 34 is shown maintaining it original tubular configuration that restricts distension as internal pressure is applied. An over-the-wire designed placement catheter 18 with expandable balloon 60 is positioned within the perfusion sleeve 16. The placement catheter is inflated and deflated using fluid pressure in lumen 62 with a second inflation lumen 68 that extends along the length of the placement catheter shaft 70. A guidewire 64 also extends along the length of the shaft 70 and extends through the placement catheter 18.

In FIG. 14, the placement catheter 18 has been retracted proximally to establish a flow channel 30 within the perfusion sleeve 16. The flexible and expandable member 24 maintains its contact with the atherosclerotic plaque 76 of vessel 50. while the semi-rigid member 34 maintains its original tubular configuration. The perfusion sleeve can remain in the vessel for an extended period of time to treat a dissection or perforation in the vessel wall.

In the mode of operation of the present invention, a typical coronary guidewire would be introduced into the patient's blood system near the groin and advanced along the aorta, with the aid of a previously place guide catheter, to the selected coronary vessel for treatment. The coronary guidewire would then be advanced across the lesion desired for angioplasty or other interventional treatment. While the placement catheter 18 is partially inflated and the perfusion sleeve fully deflated, the catheter assembly would be threaded over the guidewire and advanced until the distal end is positioned in the lesion. The placement catheter 18 would then be fully inflated to a pressure which firmly engages and supports the inside surface of semi-rigid member 34 of perfusion sleeve 16. While maintaining this pressure, the inflation lumen 28 of the perfusion sleeve 16 would be inflated to an appropriate pressure to perform an angioplasty dilatation or other interventional procedure. Should it be desired to maintain pressure against the vessel wall, the placement catheter 18 will then be deflated and retracted proximally, allowing the perfusion of blood flow from the proximal arterial segment and through the channel 30 to oxygenated myocardial tissues distal to the perfusion sleeve and treatment site.

When sufficient time has passed to tack up an dissection or occlude a perforation and it is desired to remove the perfusion sleeve 16 from the patient, the perfusion catheter, in a deflated state, is re-advanced over the guidewire and re-inserted into the flow channel 30 of the perfusion sleeve 16. The placement catheter is then partially inflated to engage the semi-rigid member 34 of the perfusion sleeve 16 and perfusion sleeve is deflated. Then, as a unit, the perfusion sleeve/placement catheter apparatus is retracted and removed from the patient.

In the alternative embodiment of the perfusion sleeve where an independent guidewire lumen and guidewire 44 is incorporated into the design, the step of re-advancing the placement catheter can be eliminated. When it is desired to remove the perfusion sleeve, the physician simply deflates the inflation lumen 28 to disengage the expandable member 24 from the vessel wall, reducing the profile of the sleeve and then, the deflated sleeve 42 is retracted along the guidewire 44.

Passive perfusion sleeve/placement catheter of the present invention has several advantages over other approaches to passive or auto perfusion. First, the large diameter of blood flow channel 30 permits relatively high blood flow, rates through sleeve 16 while the inflation lumen 28 is inflated. Second, because flow channel 30 is aligned with the primary flow axis of the artery 50, there is less trauma to the blood, and less pressure head required for blood flow. Third, the ability to maintain the position of guide wire 64 while permitting perfusion, while keeping it in a position to be reinserted and left across the stenosis when catheter 10 is withdrawn offers an important option to the physician.

Although the present invention has been described with reference to preferred embodiments, workers skilled in the art will recognize that changes may be made in form and detail without departing from the spirit and scope of the invention.

What is claimed is:

1. A perfusion sleeve/placement catheter assembly designed to treat a diseased coronary artery, the assembly comprising:

a perfusion sleeve apparatus comprising a first elongate shaft including a proximal end and a distal end, and having an inflation lumen extending along the longitudinal length of said shaft;

said perfusion sleeve apparatus further comprising a composite balloon located near said distal end, said balloon comprised of an inner semi-rigid material and an outer expandable material, said inner material and said outer material having mating surfaces at their ends which are bonded together to form said composite balloon with selective expansion, said composite balloon defining an interior which is in communication with the distal end of said inflation lumen;

said perfusion sleeve apparatus defining a blood flow channel;

a placement catheter having a second elongate shaft, said shaft having a guidewire lumen integral therewith;

said placement catheter including a second expandable balloon connected to a distal end of said second shaft, said expandable balloon of said placement catheter designed to engage an interior surface of said inner material of said composite balloon.

2. The catheter assembly of claim 1 further comprising a first manifold connected to a proximal end of said first shaft and a said manifold including at least one port.

3. The catheter assembly of claim 1 wherein said first elongate shaft includes an guidewire lumen extending along the longitudinal length of said shaft.

4. The catheter assembly of claim 1 further comprising a second manifold connected to a proximal end of said second shaft, said second shaft have an inflation lumen extending along the longitudinal length and in fluid communication with a port on said second manifold.

5. The catheter assembly of claim 1 wherein said first elongate shaft is reinforced with a support means.

6. The catheter assembly of claim 1 wherein the guidewire lumen of said second elongate shaft is contained only with the distal end of said placement catheter.

7. The catheter assembly of claim 1 wherein said mating surfaces of said inner material and said outer material are affixed by heat to form said composite balloon.

8. The catheter assembly of claim 1 wherein said mating surfaces of said inner material and said outer material are affixed by adhesive to form said composite balloon.

9. The catheter assembly of claim 1 wherein said inner material and said outer material are constructed from two different materials.

10. The catheter of claim 1 and further comprising a low friction coating on an interior surface of said inner material.

11. The catheter of claim 1 wherein the guidewire lumen has a bevelled opening at its proximal entry point.

12. A perfusion sleeve/placement catheter assembly for use in combination with a guidewire to dilate a stenosed coronary artery, the assembly comprising:

a perfusion sleeve apparatus including a first elongate shaft including a proximal end and a distal end, and having an inflation lumen extending along the longitudinal length of said shaft;

said perfusion sleeve apparatus comprising a composite balloon configured as a sleeve and located near said distal end, said balloon comprised of an inner semi-rigid material and an outer flexible material, said inner material and said outer material having mating surfaces which at their ends are bonded together to form said composite balloon, said composite balloon defining an interior which is in communication with the distal end of said inflation lumen;

said perfusion sleeve apparatus defining a blood flow channel;

a placement catheter having a second elongate shaft, said shaft having a relatively short guide wire lumen located near the distal end of said second elongate shaft; and said placement catheter including a second expandable balloon connected to a distal end of the shaft.

13. The catheter assembly of claim 12 wherein said expandable balloon of said placement catheter is designed to engage an interior surface of said inner material of said composite balloon.

14. The catheter assembly of claim 12 wherein said first elongate shaft is reinforced with a support means.

15. The catheter assembly of claim 12 wherein the guidewire lumn of said second elongate shaft is contained only with the distal end of said placement catheter.

16. The catheter assembly of claim 12 wherein said mating surfaces of said inner material and said outer material are affixed by heat to form said composite balloon.

17. The catheter assembly of claim 12 wherein said mating surfaces of said inner material and said outer material are affixed by adhesive to form said composite balloon.

18. The catheter assembly of claim 12 wherein said inner material and said outer material are constructed from two different materials.

19. The catheter assembly of claim 12 and further comprising a low friction coating on an interior surface of said inner material.

20. The catheter of claim 12 wherein the guidewire lumen has a bevelled opening at its proximal entry point.

* * * * *